United States Patent [19]
Schmit et al.

[11] Patent Number: 5,472,438
[45] Date of Patent: Dec. 5, 1995

[54] LAPROSCOPIC VACUUM DELIVERY APPARATUS FOR A DIAPHRAGM DAPER

[75] Inventors: Brian D. Schmit, Cleveland Hts; J. Thomas Mortimer, Chagrin Falls, both of Ohio

[73] Assignee: Case Western Reserve University, Cleveland, Ohio

[21] Appl. No.: 96,031

[22] Filed: Jul. 22, 1993

[51] Int. Cl.$^6$ .................................................. A61B 19/00
[52] U.S. Cl. ............................. 606/1; 128/642; 128/643; 128/898; 607/42
[58] Field of Search ...................... 128/639, 644, 128/20, 643, 898; 606/1, 129, 106, 115, 123; 294/64.1–65; 604/20, 35; 607/2, 9, 32, 38, 40, 42, 44, 46, 48

[56] References Cited

U.S. PATENT DOCUMENTS

| | | | |
|---|---|---|---|
| 3,640,270 | 2/1972 | Hoffmann | 128/643 |
| 3,720,433 | 3/1973 | Rosfelder | 294/64.1 |
| 3,858,926 | 1/1975 | Ottenhues | 294/64.1 |
| 4,899,753 | 2/1990 | Inoue et al. | 128/639 |
| 4,938,218 | 7/1990 | Goodman et al. | 128/643 |
| 4,960,133 | 10/1990 | Hewson | 128/643 |

FOREIGN PATENT DOCUMENTS

| | | | |
|---|---|---|---|
| 2742058 | 3/1979 | Germany | 128/643 |
| 3501339 | 7/1986 | Germany | 128/643 |
| 2089733 | 3/1990 | Japan | 294/64.1 |
| 9316633 | 9/1993 | WIPO | 128/643 |

OTHER PUBLICATIONS

D. K. Peterson, T. Stellato, M. L. Nochomovitz, A. F. Dimarco, T. Abelson, and J. T. Mortimer, "Electrical Activation of Respiratory Muscles by Methods Other than Phrenic Nerve Cuff Electrodes," PACE 1989; 12:854–860.

Primary Examiner—Stephen C. Pellegrino
Assistant Examiner—Glenn Dawson
Attorney, Agent, or Firm—Fay, Sharpe, Beall, Fagan, Minnich & McKee

[57] ABSTRACT

A laparoscopic vacuum delivery device is used for placing an epimysial electrode at the phrenic nerve motor point. The vacuum delivery device is adapted to hold the epimysial electrode while the electrode is introduced through a port into the abdomen during a laparoscopic procedure. The electrode is forcibly held against the diaphragm muscle surface for test stimulation using a suction ported through the delivery device. Multiple test sites may be explored by controlling the suction to and the position of the delivery device. The electrode is secured at an optimal location on the diaphragm muscle using an endoscopic stapler.

33 Claims, 7 Drawing Sheets

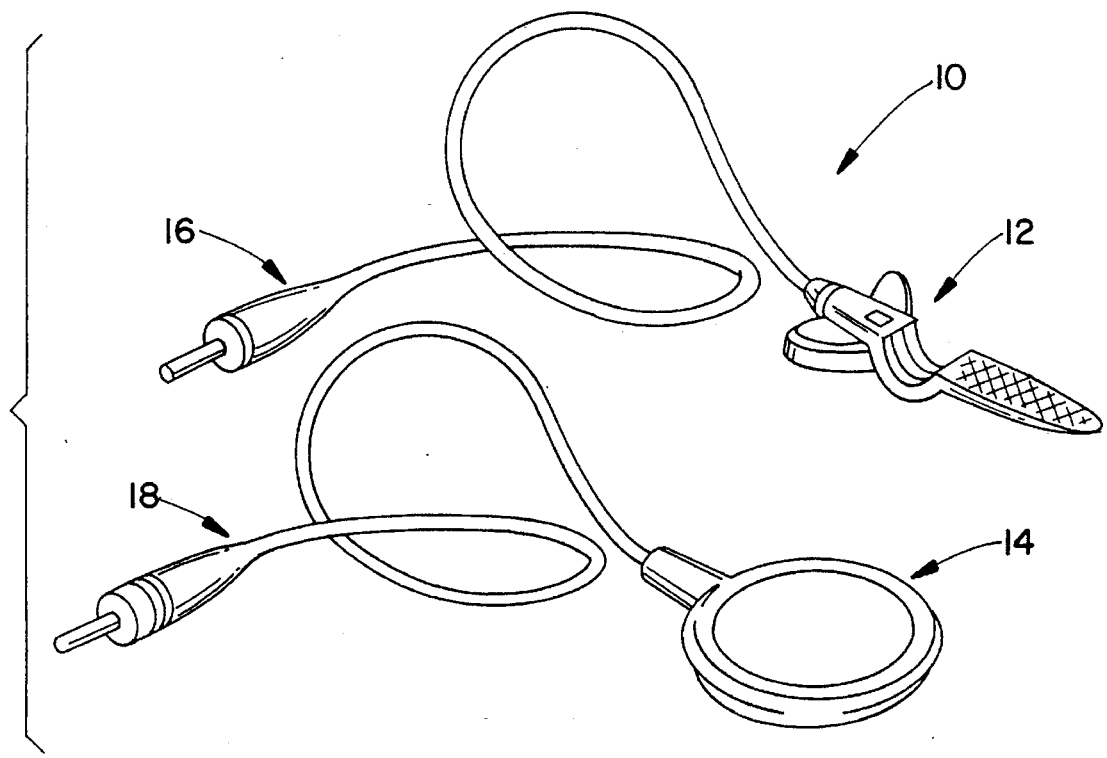
FIG. IA
(PRIOR ART)
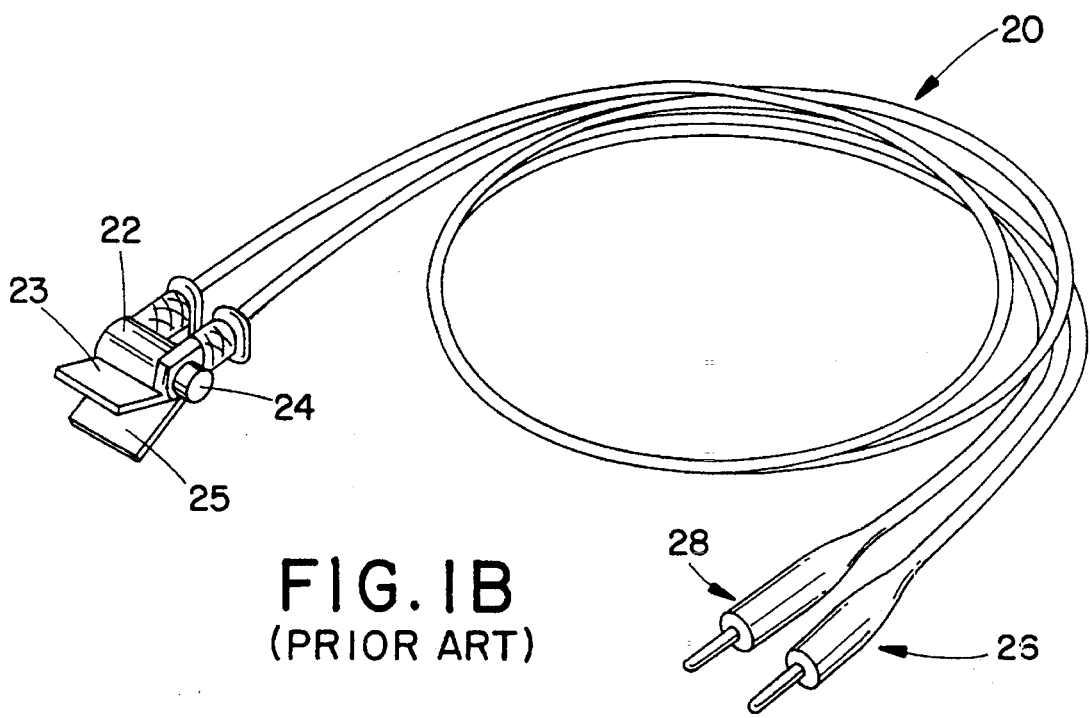
FIG. IB
(PRIOR ART)

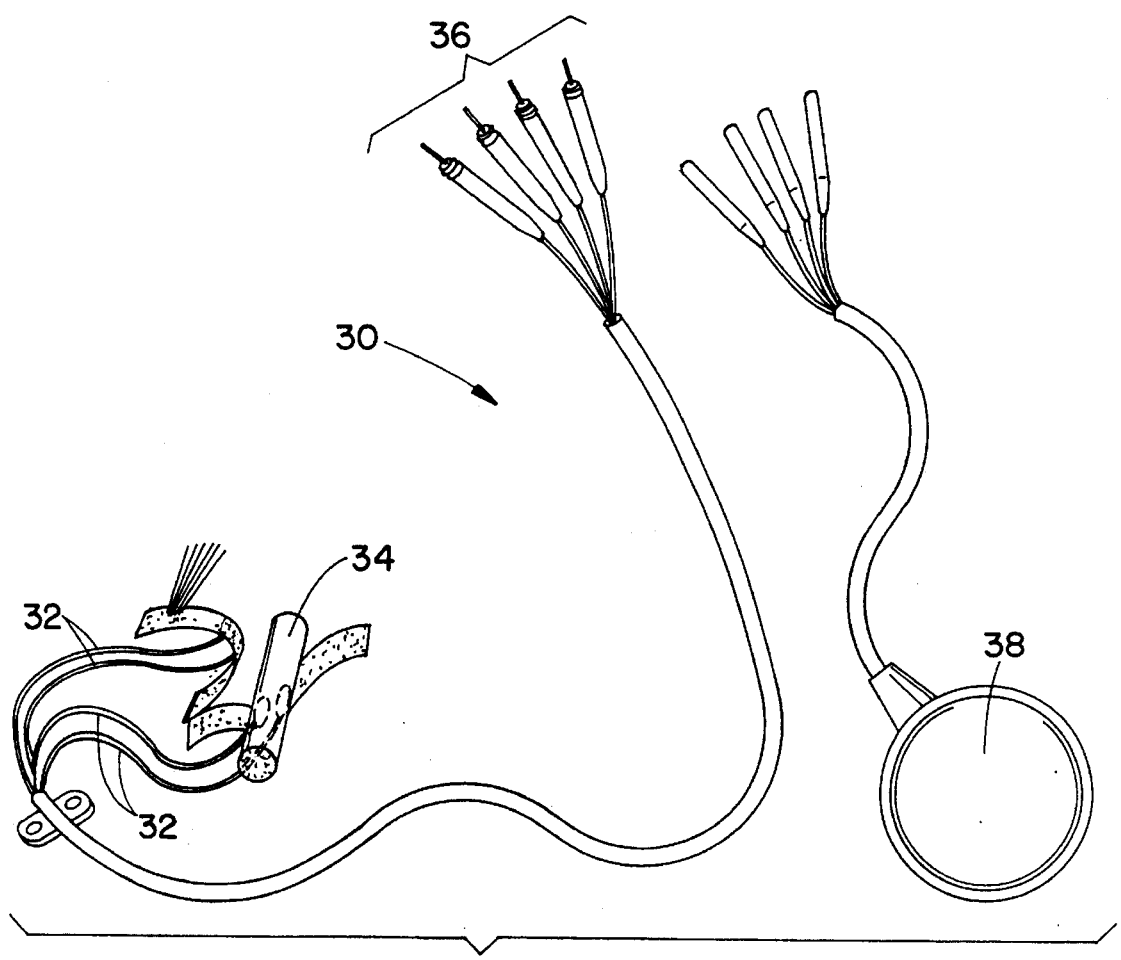
FIG. IC
(PRIOR ART)
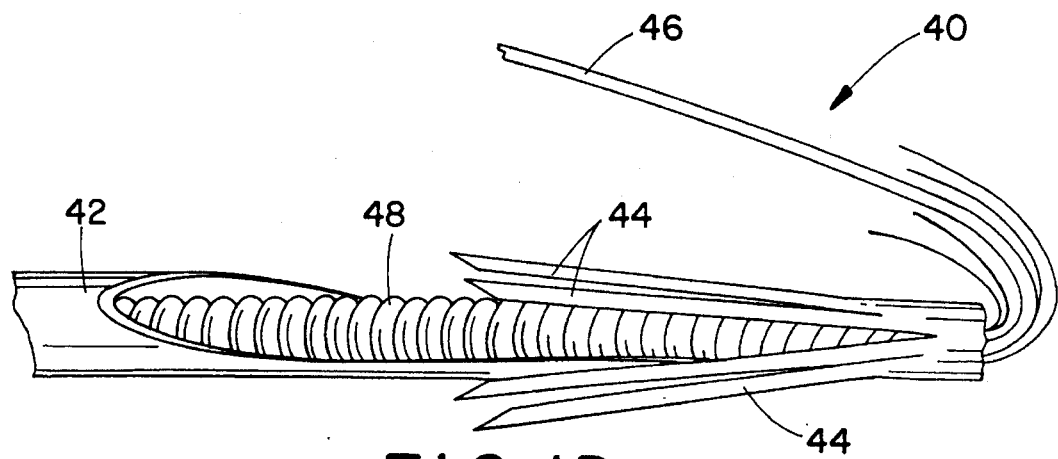
FIG. ID
(PRIOR ART)

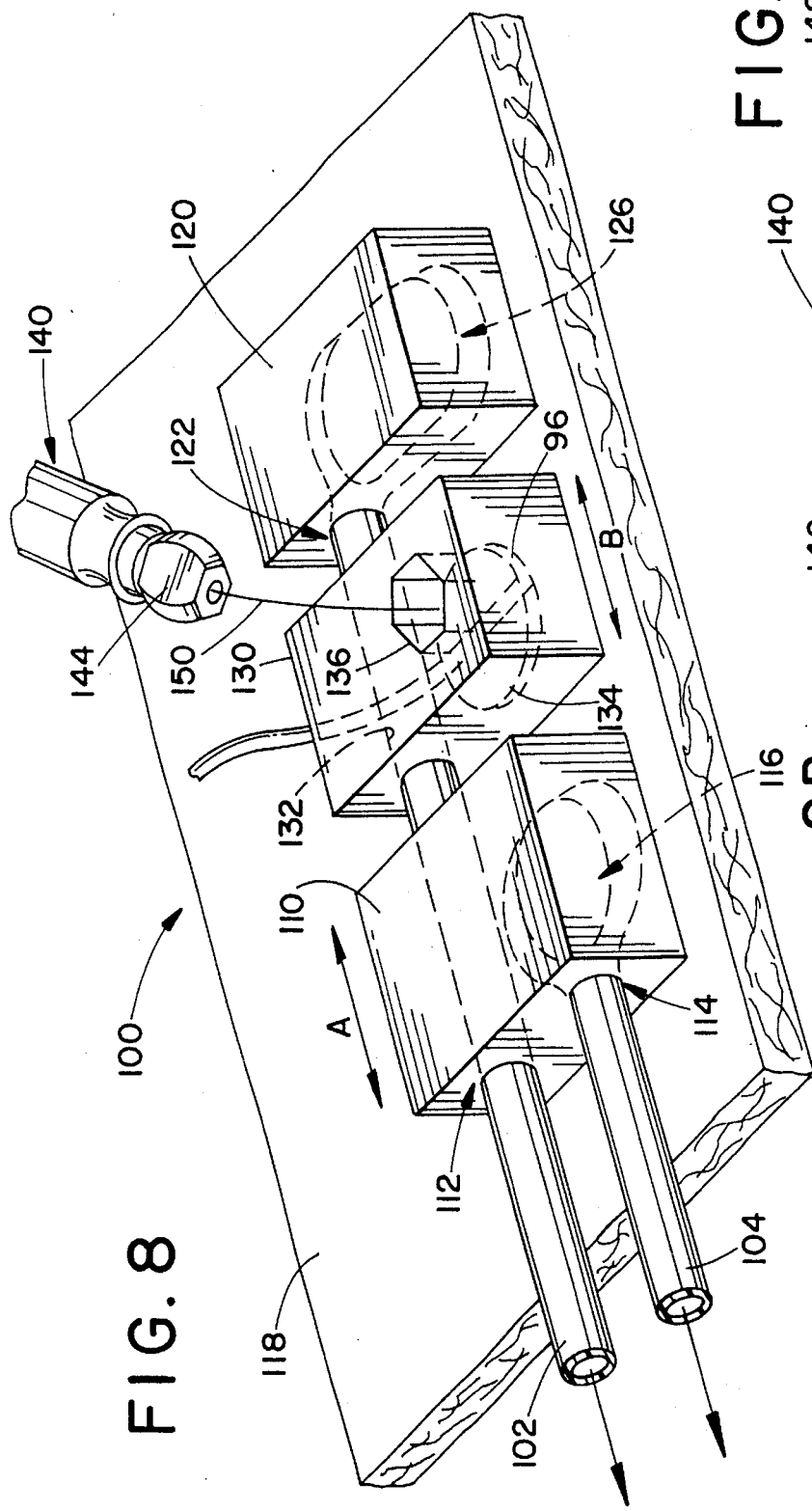
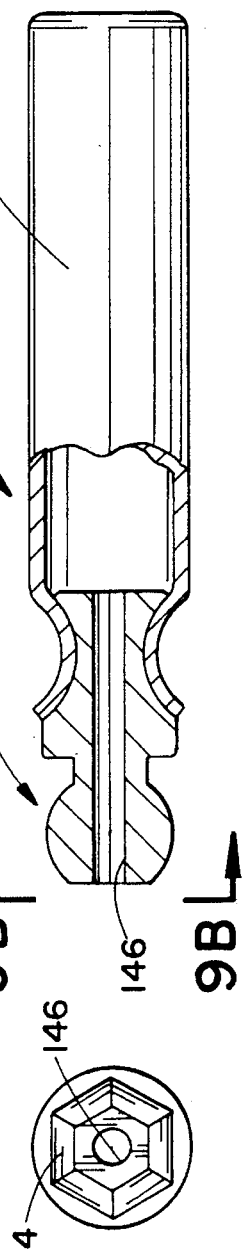

5,472,438

LAPROSCOPIC VACUUM DELIVERY APPARATUS FOR A DIAPHRAGM DAPER

BACKGROUND OF THE INVENTION

The present invention relates to the art of electrical activation of the diaphragm using epimysial electrodes.

It is to be appreciated that the invention is also applicable to control other nerve groups through electrical activation using epimysial electrodes.

It is possible to support ventilation in patients with chronic ventilatory insufficiency using a diaphragm pacer device. In broad terms, these devices pass a small amount of electric current through a pair of electrodes placed on the diaphragm muscle itself. The current passes through the diaphragm muscle thereby activating the phrenic nerves which are proximate the placement of the electrode pair, on the opposite side of the muscle. A proportion of the current may also pass through tissues other than the phrenic nerve and thus have no effect on the phrenic nerves. Since the proportion of current affecting phrenic nerve activation depends on the distance between the electrode and the phrenic nerves, electrode placement is critical. In any case, by passing the small amount of electric current through the pair of properly placed electrodes on the diaphragm muscle, the phrenic nerves are activated in turn causing a contraction of the diaphragm muscle, the primary muscle used for breathing. The diaphragm muscle contraction draws air into the lungs and the patient is ventilated. Although the above approach appears to be simple, past attempts at diaphragm pacing have met with limited success for a variety of reasons.

The general idea of stimulating the phrenic nerve for ventilation was investigated by Sarnoff in the late 1940's (Sarnoff 1948). Sarnoff's work was made a clinical reality by Glenn in the 1960's (Glenn 1973, Glenn 1988). In those systems, the electrodes are "cuffs" made of silicon rubber with platinum stimulating surfaces which are placed directly on the nerve in the neck or thorax. The electrodes themselves may be unipolar or bipolar but the current trend is to implant electrodes of the unipolar type. FIG. 1A illustrates a unipolar electrode 10 for diaphragm pacing. FIG. 1B illustrates a bipolar electrode 20 also for diaphragm pacing. The unipolar electrode 10 includes a first electrode 12 for placement around the phrenic nerve and an anode 14 located somewhere in the body of the patient. A pulse of current is applied to a first connector 16, through the first electrode 12. The current passes through the body tissues into the anode 14 and out of the diaphragm pacing system 10 through a second connector 18. A reversal of the above-described flow occurs for a second current pulse immediately following the first. After a short delay, the pair of current pulses is repeated. This repetition continues as long as diaphragm muscle contraction is desired. Current flowing from the first electrode 12 to the anode 14 or from the anode 14 and to the first electrode 12 stimulates the phrenic nerves inbetween.

FIG. 1B illustrates a bipolar electrode wherein a first electrode 22 is electrically isolated from a second electrode 24 using suitable insulating material. As illustrated in the FIGURE, the phrenic nerve is held between the first and second electrodes 22, 24 by placing a suture in the electrode extensions 23, 25. The first electrode 22 is connected to a first connector 26 and the second electrode 24 is connected to a second connector 28. As with the system illustrated in FIG. 1A, current may be applied between the electrode pair 22, 24 in either polarity for suitable activation of the phrenic nerves.

Although the above-described systems perform adequately, a number of problems exist. One problem is that the implant procedure for installing either the unipolar electrode 10 or the bipolar electrode 20 is difficult and invasive. Also, the electrodes themselves impose a risk of irreversible damage to the phrenic nerve through contact therewith. As a result, the devices of FIGS. 1A and 1B have not been well accepted in the medical community. Unfortunately, as a result, the full potential of diaphragm pacing has not been realized through the reluctance to accept these devices.

Another diaphragm pacer is illustrated in FIG. 1C. This pacer 30 uses a similar type of electrode as the device of FIG. 1A placed in a similar location at the phrenic nerve. However, the pacer 30 illustrated in FIG. 1C uses four electrodes 32 placed around the phrenic nerve 34 in a manner slightly different than that possible with the unipolar electrode 10 or the bipolar electrode 20. The main difference in the system illustrated in FIG. 1C is that a four pole sequential nerve stimulation is possible through selective stimulation of pairs of electrodes 32. Also, the pacer 30 is capable of changing anode and cathode configurations of the electrodes during stimulation. Although the pacer 30 offers significant advantages over the earlier described systems, the basic problems remain including the difficulty in implanting the apparatus, the invasive nature of the surgery and the possible risk of irreversible damage to the nerve.

Accordingly, other systems have been developed for electrical activation of respiratory muscles by methods other than phrenic nerve cuff electrodes. Some of these systems are described in "Electrical Activation of Respiratory Muscles by Methods Other Than Phrenic Nerve Cuff Electrodes", D. K. Peterson, T. Stellato, M. L. Nochomovitz, A. F. DiMarco, T. Abelson and J. T. Mortimer, Diaphragm Stimulation Symposium at Cardiostim 1988, Jun. 15–18, 1988, pages 854–860.

With reference now to FIG. 1D, a prior art intramuscular diaphragm stimulating electrode is illustrated. The electrode is shown, extending from the tip of a hypodermic needle 42. The electrode itself is comprised of a polymer barb set 44, a monofilament barb 46 and a coiled multistrand stainless steel wire with teflon insulation. The insulation of the wire ends at the barbs allowing electrical contact between the bare wires and the surrounding tissue. The polymer barb set 44 and the monofilament barb 46 are connected to an associated electrical stimulating device by an extension of the monofilament that passes through the center of the coil of wire 48. The wire 48 carries current from the electrical apparatus to the polymer barb set and the monofilament barb.

In use, the intramuscular diaphragm stimulating electrode 40 is urged down through the hollow body of a hypodermic needle far enough to permit the monofilament barb 46 to spring radially away from the wire 48. The wire is then retracted leaving only the monofilament barb exposed at the tip of the hypodermic needle. The monofilament barb indicates the depth of the needle insertion into the diaphragm during device implant. Although this system provides excellent results, placement of the electrode itself is critical to the success of the procedure. To help with placing the electrode, a laparoscope is inserted into the abdominal space and the surface of the diaphragm itself is observed to locate an appropriate implant site. Optimal theoretical placement of the electrode is known using a "map" of the diaphragm based on anatomical landmarks. However, it is often impossible to tell between patients which point would be most optimal because anatomical landmarks are patient dependent. However, equipped with the barbed intramuscular diaphragm stimulating electrode 40 illustrated in FIG. 1D, surgeons do not have the luxury of multiple attempts at locating an optimal site.

The present invention contemplates a new and improved technique for phrenic nerve stimulation and location of implant sites for diaphragm pacing electrodes.

SUMMARY OF THE INVENTION

In accordance with one aspect of the present invention, an electrode configuration is provided for establishing uniform current densities between the electrode and tissue immediately adjacent the electrode.

In accordance with another aspect of the present invention, an apparatus and method are provided whereby an electrode is placed in intimate contact with the diaphragm muscle and held in place by a vacuum. An electrical current is applied to the electrode such that the muscle activation may be observed.

In this manner a method of locating an optimal electrode implant site on the diaphragm is provided. The electrode is connected to an associated vacuum assist delivery device which maintains the electrode in close contact with the diaphragm muscle for test stimulation. Movement of the electrode over the diaphragm is possible through controlled vacuum application.

One advantage of the present invention is that it enables surgeons to locate an optimal electrode implant site without damage to the diaphragm muscle.

Another advantage of the present invention is that the current densities through the electrode are maintained to be uniform.

Another advantage of the present invention is that a tethered wrench is provided for manipulation by the surgeon for translation and rotation of the vacuum assist delivery device over the diaphragm muscle.

Still further advantages of the present invention will become apparent from the following detailed description.

BRIEF DESCRIPTION OF THE DRAWINGS

The invention may take form in certain parts and arrangements of parts, and in various steps and arrangements of steps. The drawings are only for purposes of illustrating the invention and are not to be construed as limiting it.

FIGS. 1A–1D are elevational views of prior art phrenic nerve stimulation apparatus;

FIG. 8 is a perspective view illustrating the vacuum delivery device for use with a diaphragm pacer according to the present invention; and, FIGS. 9A and 9B are partial cutaway side and end profile views of the wrench used with the vacuum delivery device of the present invention illustrated in FIG. 8.

DETAILED DESCRIPTION OF THE PREFERRED EMBODIMENT

Figure 2A:
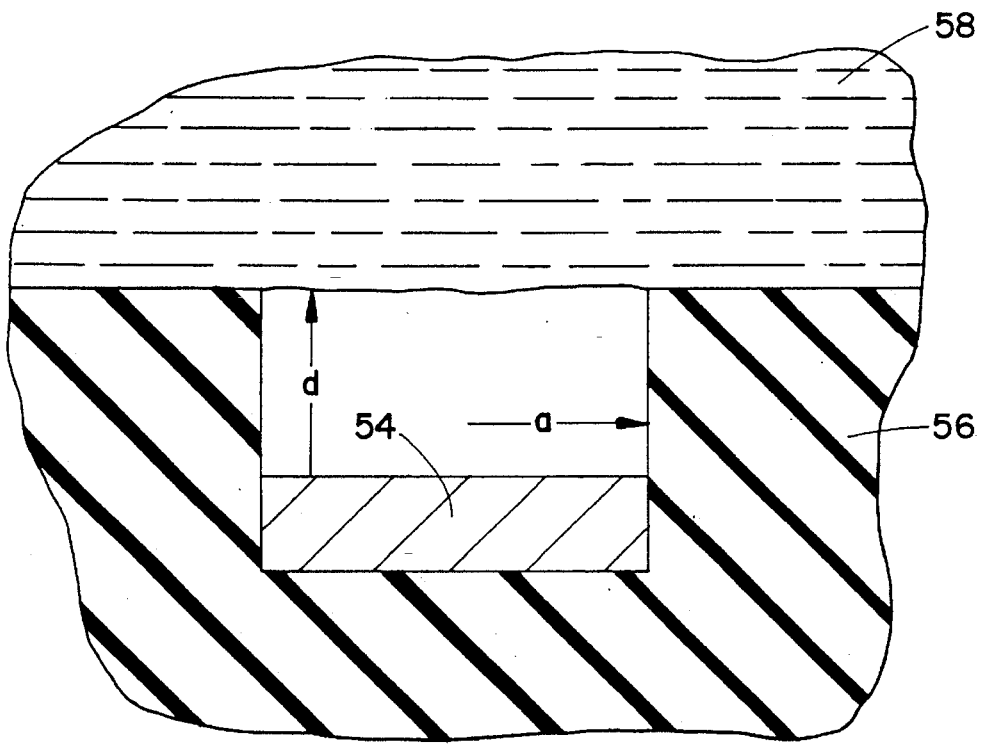
FIGS. 2A and 2B are cross-sectional illustrations of the electrode configurations used with the diaphragm pacer of the present invention to provide uniform current density.
Figure 2B:
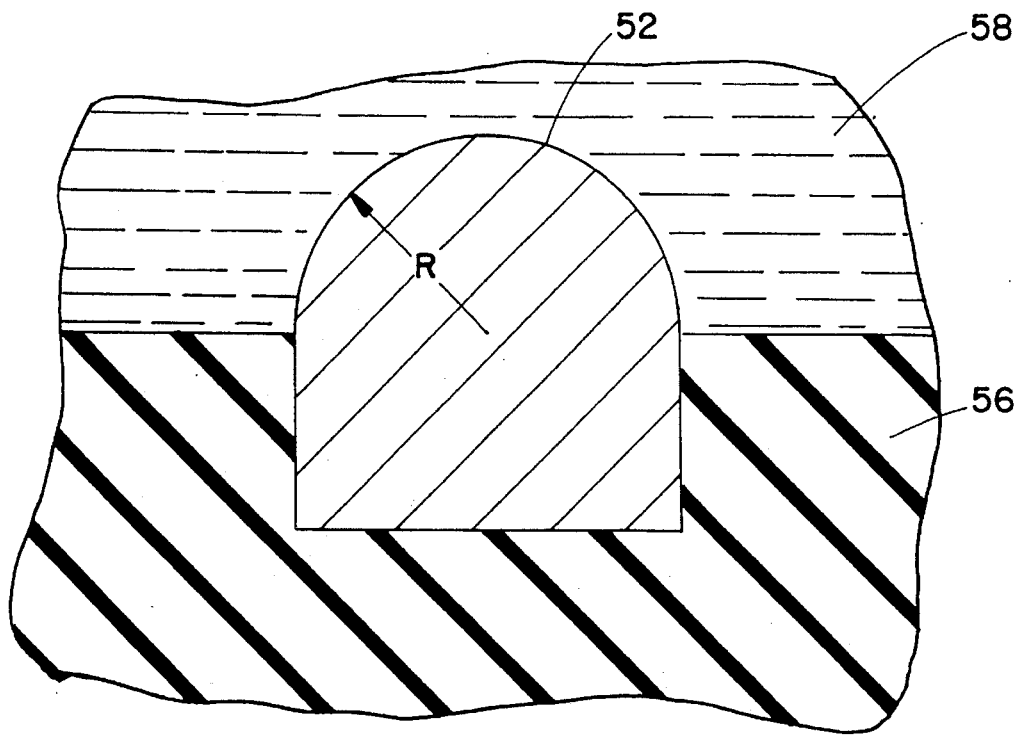

With reference to FIGS. 2A and 2B, the stimulating surface of the electrode comprising the ventilator prosthesis of the present invention may be either hemispherical 52 or a flat surface 54 within a well of insulator material 56. In either case, the current density of the electrodes 52, 54 with respect to the surrounding tissue, represented in the FIGURES as a saline solution 58, is critical. Uniform current density through the electrode surface prevents corrosion of the electrode and reduces damage to the tissue. To reduce current density and make a more reliable electrode, the surface area of the electrode contacting the tissue is 10 mm$^2$. A maximum current amplitude of 20 milliamps at a maximum frequency of 50 Hz, having a pulse width of less than 200 microseconds can be used safely for an electrode with a surface area of 10 mm$^2$.

Each of the electrodes 52, 54 illustrated in the FIGURES are formed of stainless steel. The electrodes could be formed of iridium oxide to increase the safety factor for the above stimulus parameters. The circular stimulation surface of the hemispherical electrode 52 is preferably 1.75 mm in radius wherein a 10 mm$^2$ surface area is provided. In any case, each of the electrodes 52, 54 are generally encapsulated in an insulating material 56 and have a surface area carefully selected according to an intended stimulation signal. Since the surface conducts electricity between the electrode and the tissue, prevention of corrosion and reduced damage to the tissue is of utmost importance.

Figure 3A:
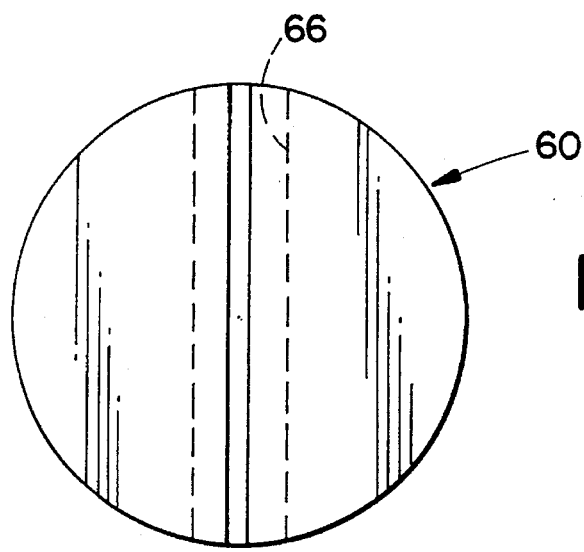
FIGS. 3A–3C are top, front and side profile views of a disk used as the stimulating electrode surface of the present invention.
Figure 3B:
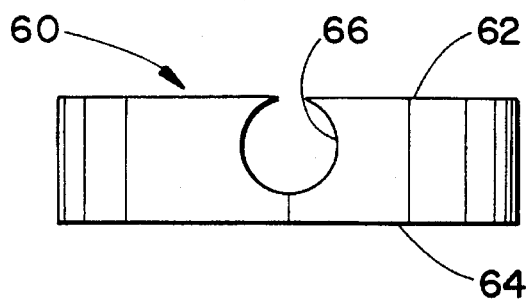
Figure 3C:
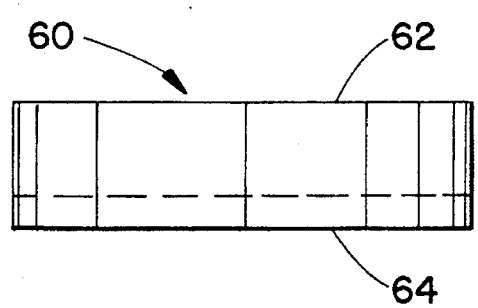
Figure 4A:
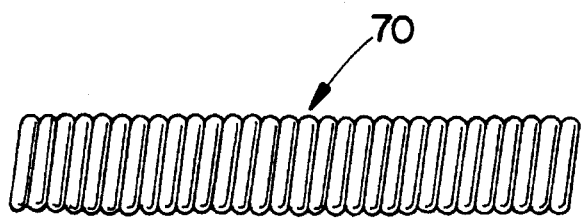
FIGS. 4A and 4B are side and profile views of the strain relief coil used for the epimysial electrode of the present invention.
Figure 4B:
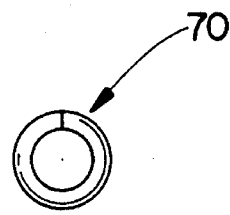
Figure 5A:
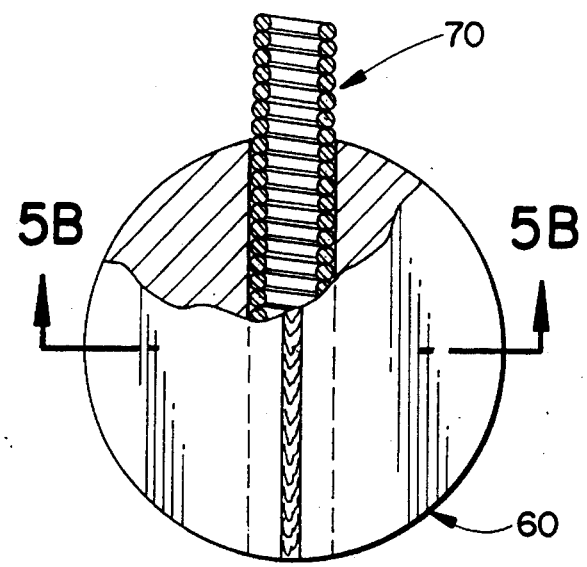
FIGS. 5A–5C are a top partial cutaway views of the disk and strain relief coil assembly of the present invention, and cross-sectional front and side views of the disk and strain relief coil assembly of the present invention.
Figure 5B:
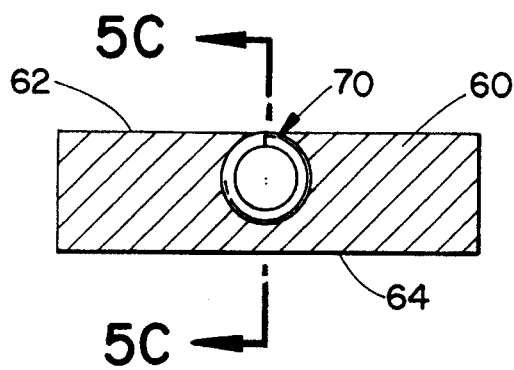
Figure 5C:
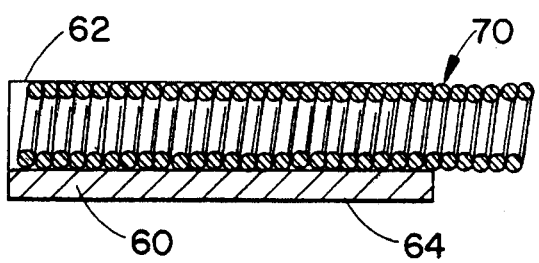

With reference now to FIGS. 3A–3C, the stimulating surface of the diaphragm pacer of the preferred embodiment is illustrated as being formed of a disk 60. The disk is generally circular having a flat top 62 and bottom 64 for the electrode with a stimulating surface in a well. The electrode with a hemispherical stimulating surface has a hemispherical protrusion on the bottom surface. A transverse bore 66 is provided running entirely through the disk 60. The bore is appropriately sized to receive a strain relief coil 70 as illustrated in FIGS. 5A and 5C. The strain relief coil 70 (FIGS. 4A, 4B) is received into the bore 66 (FIGS. 5A–5C) but leaving a slight amount of the strain relief coil extending from the bore in a "pigtail" configuration. The end of the strain relief coil 70 opposite the pigtail is confined to remain within the disk 60 such that the strain relief coil 70 extends from the disk 60 only on a single end. The strain relief coil 70 is fixed in this position in the bore 66 by a weld of the two pieces.

Figure 6:
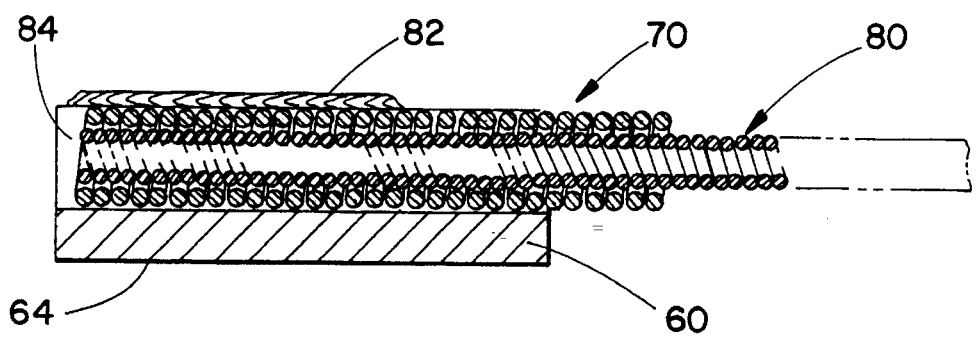
FIG. 6 is a detailed, cross-sectional illustration of the disk and coil assembly of FIGS. 5A–5C with a lead wire assembly attached thereto.

With reference next to FIG. 6, the disk 60 with the strain relief coil 70 received therein, is further provided with a coiled lead wire 80 co-axially received within the strain relief coil 70. In the preferred embodiment, the coiled lead wire 80 is a multistranded stainless steel wire. The multistranded stainless steel wire is ideally suited for carrying current from a stimulator apparatus to the stimulating surface 64 of the disk 60. With continued reference to FIG. 6, the coiled lead wire 80 is formed into a helix having insulation removed from one end thereof (left end in FIG. 6). The helical wire 80 is passed through the strain relief coil 70 and the deinsulated wire is connected to the disk coil assembly at 82. Since the coiled lead wire of the preferred embodiment is very fine, the strain relief coil 70 as illustrated in the FIGURE is used to discourage severe bends at the area where the wire 80 meets the disc 60. That is, the coiled lead wire 80 is surrounded by the strain relief coil 70 as both exit from the bore 66 of the disk 60. A polypropylene monofilament plug 84 is inserted coaxial with both the strain relief coil 70 and the coiled lead wire 80. The coiled lead wire 80 is suitably provided with a deinsulated segment which is passed through the strain relief coil 70 and welded to the disk 60 at a weld joint 82. Once welded, the polypropylene plug 84 is inserted to prevent transfer of longitudinal stresses on the coiled lead wire to the weld joint 82.

Figure 7A:
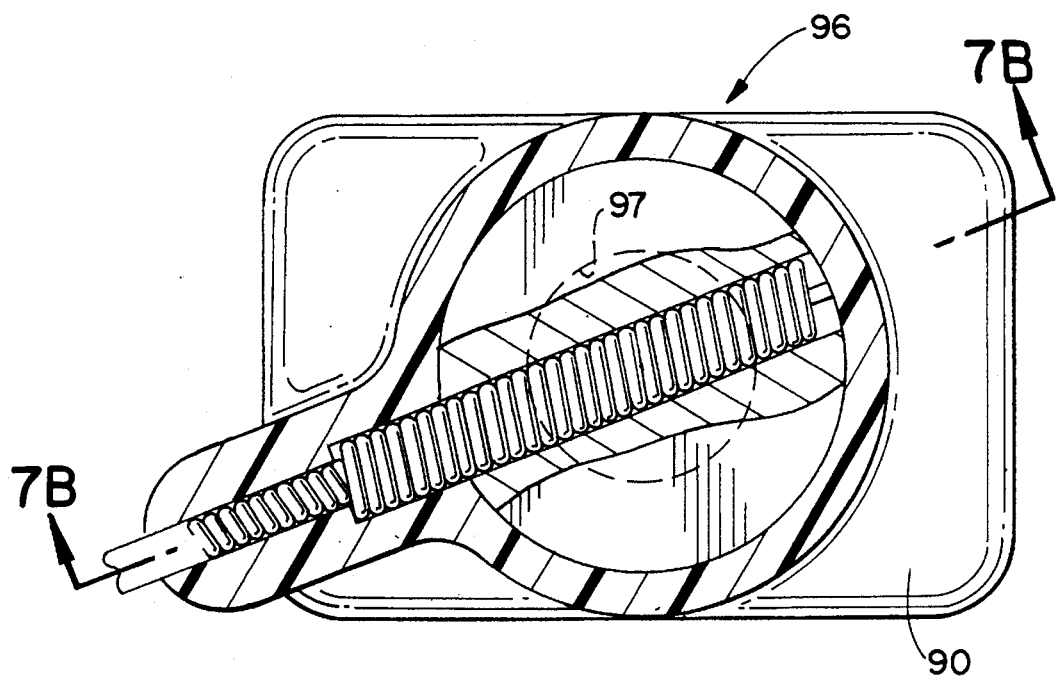
FIGS. 7A and 7B are top and detailed cross-sectional views of the overall assembly enclosed in a silicon rubber housing.
Figure 7B:
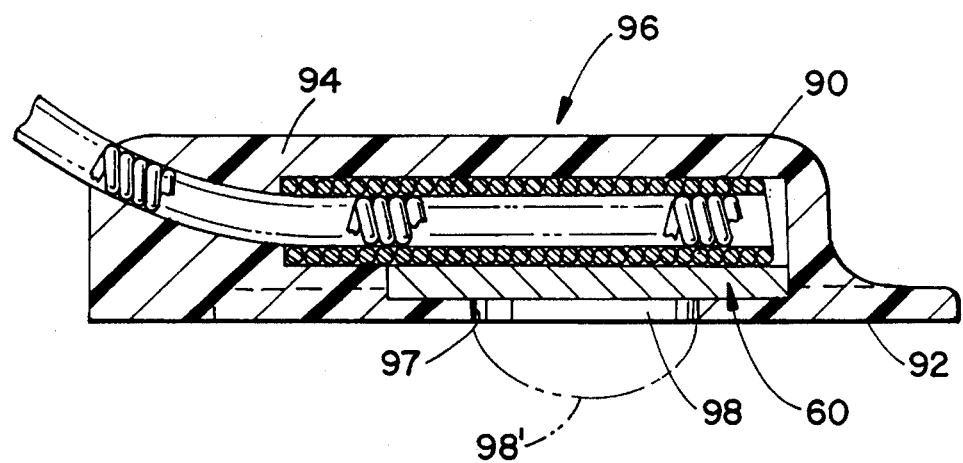

The last step in the fabrication of the diaphragm pacer, with reference to FIGS. 7A and 7B, is encasement of the entire assembly illustrated in FIG. 6 in a silicone rubber form 90 having a flat bottom surface 92 and a strain relief portion 94. It is to be noted that the diaphragm pacer electrode assembly 96 illustrated in FIGS. 7A and 7B has a stimulating surface formed of the type illustrated in FIG. 2A. That is, the stimulating surface of the device 96 is a flat surface 98 of the bottom 64 of the disk 60 (FIG. 6). The well walls 97 are formed by the silicone covering 90 to a desired depth d illustrated in FIG. 2A. Also, as shown in FIG. 7A, the well is circular having a radius a as shown in FIG. 2A.

It is to be further noted that the electrode assembly 96 may also be formed around a suitably shaped bottom surface 64 of the disk 60 comprising a hemispherical electrode surface such as illustrated in FIG. 2B. In that case, the hemispherical surface would extend beyond the bottom 92 of the assembly 96 as illustrated by the dashed line 98' which is exaggerated for the purpose of illustration.

FIG. 8 illustrates the vacuum delivery device 100 for laparoscopic implant of the diaphragm pacer. In general, the vacuum delivery device 100 provides a means of placing the epimysial electrode at the optimal point on the muscle for phrenic nerve stimulation. The vacuum delivery device 100 is designed to carry the epimysial electrode through a port and into the abdomen during a laparoscopic procedure, and hold the electrode tightly against the diaphragm muscle surface for testing phrenic nerve activation. The vacuum delivery device provides testing at many potential implant sites because the electrode can be secured, released and resecured to many locations on the muscle surface. When the implant site is identified, the vacuum delivery device holds the electrode tightly against the diaphragm muscle until it can be secured using an endoscopic stapler (not shown). Suction provides the temporary holding mechanism and the movement of the epimysial electrode is controlled by the surgeon using a specialized tool which will be described in greater detail below.

With continued reference to FIG. 8, the vacuum delivery device 100 includes three (3) basic members. The first member 110 is rectangular having continuous surfaces on three sides. A left side surface of the first member 110 as viewed in FIGURE is adapted to receive a first vacuum tube 102 at a first opening 112 and to fixedly receive a second vacuum tube 104 at a second opening 114. The first opening 112 is merely an enlarged bore through the first member 110 sized slightly larger than the outer diameter of the first vacuum tube 102. The first member 110 is provided on a bottom surface as viewed in the drawing with a first vacuum port 116. The vacuum port 116 presents a cavity toward the surface of the diaphragm muscle. The diaphragm is represented in the FIGURE as a planar surface 118. As can be seen in the FIGURE, the first vacuum port 116 is connected through second port 114 to the second vacuum tube 104. Fluid suction as by the application of a suitable vacuum apparatus to the second vacuum tube 104 causes the first member 110 to adhere to the surface 118 due to the suction at the first vacuum port 116.

A second vacuum port 126 is provided on the bottom of a second member 120 as viewed in the FIGURE. The second vacuum port 126 opens towards the surface 118 of the tissue. The second member 120 is ported to receive the first vacuum tube 102 at an opening 122. Both vacuum tubes 102, 104 are suitably connected to the first and second members 110, 120, by an adhesive glue, a weld, or the like.

The vacuum delivery device 100 illustrated in FIG. 8 includes a third member 130 having a bore therethrough 132 which is suitably sized to be slightly larger than the outer diameter of the first vacuum tube 102. Also, the third member 130 is provided, on the bottom as viewed in the FIGURE, with a suitable cavity 134 to receive the electrode 96 illustrated in FIGS. 7A and 7B. The electrode fits closely and is releasable from the cavity 134. The top of the third member 130 defines a hexagonal opening 136 receiving a corresponding ball head hexagonal wrench 140.

With reference to both FIGS. 8 and 9A–9B, the use of the hexagonal wrench 140 with the vacuum delivery device 100 will be described. In general, the ball head hexagonal wrench 140 includes a male hexagonal tip portion 142 defining a spherical hexagonal male member 144. The spherical hexagonal male member on the tip 142 is provided with a bore receiving a tether 150 which is secured on one end to the third member 130 of the vacuum delivery device generally denoted as 100. In the preferred embodiment, the tether 150 is a polypropylene filament.

The major portion of the ball head hexagonal wrench is formed from a 316 L stainless steel rigid tube 148. The tether 150 is secured on one end to the third member 130 and is threaded through both the head 142 and the elongate portion 148 of the ball head hexagonal wrench and beyond.

Broadly viewed, the vacuum delivery device 100 defines an overall flexible housing as provided by the spaced-apart and separate first, second and third members 110, 120 and 130 respectively. Collectively, the first through third housing members are arranged on a first side for releasable attachment to the diaphragm pacer electrode 96. The first side of the composite housing further includes a plurality of vacuum ports 116 and 126 for communicating vacuum from the hoses 104 and 102 respectively, to the operatively associated diaphragm surface 118.

In use, the apparatus illustrated in FIGS. 8 and 9A–9B provides a surgeon with positive control over the placement of the electrode assembly 96 through the operation of the first and second vacuum tubes 102, 104 and the ball head hexagonal wrench 140. In particular, the apparatus is inserted into the abdominal cavity with the ball head hexagonal wrench 140 received into the hexagonal opening 136 of the third member 130. Upon finding a first appropriate location on the surface of the diaphragm muscle, the vacuum is applied to the first and second vacuum tubes 102, 104, causing the first and second members 110, 120 to stick to the surface 118 of the tissue due to the suction in the first and second vacuum ports 116, 126. Next, with the vacuum on the tubes 102, 104 being maintained, the ball head hexagonal wrench 140 is withdrawn from engagement with the third member 130. According to the description above, the ball head hexagonal wrench 140 remains only loosely connected to the third member 130 through the tether 150. The tether being formed of polypropylene filament is flexible enough to permit movement of the first, second and third members 110, 120, and 130 on the surface 118 of the tissue without the influence of the rigid ball head hexagonal wrench 140. Then, current is passed through the electrode causing the diaphragm muscle to move separate and apart from the ball head hexagonal wrench 140. The quality of the selected stimulation point is thereby evaluated without the influence of the wrench 140.

In the event that the selected point is of marginal or poor quality judging from the diaphragm's response to the electrical stimulation, the ball head hexagonal wrench 140 is reinserted into the third member 130. Insertion of the ball head hexagonal wrench is guided by the tether 150 by grasping the tether extending beyond the tube 148 (not shown) and sliding the tube over the tether toward the third member 130 and into the socket 136. This procedure is performed while maintaining the vacuum applied to the first and second vacuum tubes 102, 104.

Once the ball head hexagonal wrench 140 is secured into the third member 130, the suction is removed from the vacuum tubes 102, 104 causing the first and second members 110, 120 to release their grip caused by the suction on the surface 118 of the diaphragm muscle. The first, second and third members 110, 120, and 130 connected directly to the ball head hexagonal wrench 140 and indirectly through the first vacuum tube 102 are translatable and/or rotatable by the surgeon merely by manipulating the tube 148 of the wrench 140. This procedure is repeated until the optimal placement point is located whereupon the electrode assembly 96 is stapled to the diaphragm using an endoscopic stapler (not shown).

The invention has been described with reference to the preferred embodiment. Obviously, modifications and alterations will occur to others upon reading and understanding the preceding detailed specification. It is intended that the invention be construed as including all such alterations and modifications insofar as they come within the scope of the appended claims or the equivalents thereof.

Having thus described the preferred embodiment, the invention is now claimed to be:

1. A vacuum delivery apparatus for laparoscopic implant of an operatively associated diaphragm pacer, the apparatus comprising:
   a first housing adapted on a first side for releasable attachment to said operatively associated diaphragm pacer;
   a second housing connected to said first housing and including:
   first vacuum source connection means for connecting the second housing to a first operatively associated vacuum source; and,
   first port means defining a first opening on a first side of the second housing in fluid communication with said first vacuum source connection means; and,
   a third housing connected to said first housing and including:
   second vacuum source connection means for connecting the third housing to a second operatively associated vacuum source; and,
   second port means defining a second opening on a first side of the third housing in fluid communication with said second vacuum source connection means.

2. The apparatus according to claim 1, wherein: said first port means is adapted to communicate vacuum from said first operatively associated vacuum source to the first side of the second housing through the first vacuum source connection means; and,
   said second port means is adapted to communicate vacuum from said second operatively associated vacuum source to the first side of the third housing through the second vacuum source connection means.

3. The apparatus according to claim 2, wherein the first side of the first housing, the first side of the second housing and the first side of the third housing are substantially disposed in a single plane.

4. The apparatus according to claim 3 further comprising:
   a first elongate vacuum tube, connected between said first vacuum source connection means and said first operatively associated vacuum source, for communicating vacuum from said first operatively associated vacuum source to said second housing; and,
   a second elongate vacuum tube, connected between said second vacuum source connection means and said second operatively associated vacuum source, for communicating vacuum from said second operatively associated vacuum source to said third housing.

5. The apparatus according to claim 4 further comprising:
   first connecting means for loosely connecting said second housing to said first housing; and,
   second connecting means for loosely connecting said third housing to said first housing.

6. The apparatus according to claim 5, wherein said first and second connecting means comprise said first elongate vacuum tube.

7. The apparatus according to claim 6, wherein said first housing and said third housing are both adapted to loosely receive said first vacuum tube.

8. The apparatus according to claim 7 further comprising:
   a manual positioning member;
   an interface defined by said first housing, the interface being adapted to releasably receive a first end of said manual positioning member; and,
   tether means attached to said interface defined by said first housing.

9. The apparatus according to claim 8, wherein said manual positioning member is adapted on said first end to axially receive said tether means.

10. The apparatus according to claim 9, wherein said interface includes a first keyed portion and said manual positioning member includes a second keyed portion adapted for selective mated coupling with said first keyed portion.

11. The apparatus according to claim 9, wherein said manual positioning member is adapted to axially receive said tether means for the length of the manual positioning member.

12. The apparatus according to claim 1 further comprising:
    a manual positioning member;
    an interface defined by said first housing, the interface being adapted to releasably receive a first end of said manual positioning member; and,
    tether means attached to said interface defined by said first housing.

13. The apparatus according to claim 12, wherein said manual positioning member is adapted on said first end to axially receive said tether means.

14. The apparatus according to claim 13, wherein said interface includes a first keyed portion and said manual positioning member includes a second keyed portion adapted for selective mated coupling with said first keyed portion.

15. The apparatus according to claim 14, wherein said manual positioning member is adapted to axially receive said tether means for the length of the manual positioning member.

16. A laparoscopic pacer placement apparatus comprising:
a diaphragm pacer;
a collective arrangement of relatively moveable connected portions, the arrangement including pacer connecting means in the form of a pocket on a first side of the collective arrangement selectively releasably attaching to said diaphragm pacer;
vacuum source connection means adapted to connect said collective arrangement to an operatively associated external vacuum source; and,
means defining an opening on said first side of the collective arrangement, the opening defining means in fluid communication with said vacuum source connection means and adapted to communicate vacuum from said associated vacuum source to diaphragm tissue adjacent said arrangement through said opening.

17. The apparatus according to claim 16, wherein said collective arrangement comprises first, second and third portions.

18. The apparatus according to claim 17, wherein said first, second and third portions are first, second and third rigid members respectively, loosely connected for an overall flexibility of said collective arrangement.

19. The apparatus according to claim 16, wherein said collective arrangement is adapted to move in substantial correspondence with movement of said diaphragm tissue.

20. The apparatus according to claim 16, wherein said collective arrangement includes independently moveable portions.

21. A vacuum delivery device for laparoscopic implant of an associated diaphragm pacer, the device comprising:
a first member connected to a first operatively associated external vacuum source;
a first vacuum port on the first member connected to the first vacuum source;
a second member connected to the first member and adapted for releasable attachment to the associated diaphragm pacer;
a third member connected to the second member and connected to a second operatively associated external vacuum source; and,
a second vacuum port on the third member connected to the second vacuum source.

22. The device according to claim 21, wherein:
the first port is adapted for communicating vacuum from the first vacuum source; and,
the second port is adapted for communicating vacuum from the second vacuum source.

23. The device according to claim 22, wherein the first and second vacuum ports are disposed in a single plane.

24. The device according to claim 22 further comprising:
first vacuum communicating means for communicating vacuum from the first vacuum source to the first member; and,
second vacuum communicating means for communicating vacuum from the second vacuum source to the third member.

25. The device according to claim 24 further comprising means for connecting the first member to the second member and means for connecting the second member to the third member.

26. The device according to claim 25, wherein the means for connecting the first member to the second member and the means for connecting the second member to the third member comprise the second vacuum communicating means.

27. The device according to claim 26 further comprising:
a manual positioning member;
an interface slot defined by the second member, the interface slot being adapted to releasably receive a first end of said manual positioning member; and,
a tether attached to the interface slot.

28. The device according to claim 27, wherein said manual positioning member is adapted on said first end to axially receive said tether.

29. The device according to claim 28, wherein said interface slot includes a first keyed portion and said manual positioning member includes a second keyed portion adapted for selective mated coupling with said first keyed portion.

30. The device according to claim 28, wherein said manual positioning member is adapted to axially receive said tether means for the length of the manual positioning member.

31. The device according to claim 21 further comprising:
a manual positioning member;
an interface defined by the second housing, the interface being adapted to releasably receive a first end of said manual positioning member; and,
tether means attached to said second housing at said interface.

32. A method for laparoscopically placing an electrode at an optimal site on a body tissue comprising:
a) receiving an electrode on a first side of a vacuum delivery apparatus;
(b) placing the vacuum delivery apparatus through a laparoscopic port and into a body;
c) positioning the first side of the vacuum delivery apparatus on a body tissue at a first site;
d) vacuum attaching the vacuum delivery apparatus to the body tissue by connecting the vacuum delivery apparatus to an operatively associated external source of vacuum; and,
e) during said vacuum attaching, applying an electrical signal to said electrode to stimulate the body tissue.

33. The method according to claim 32 further comprising the steps of:
f) releasing the vacuum delivery apparatus from the body tissue by disconnecting the apparatus from said operatively associated external source of vacuum;
g) repositioning the first side of the vacuum delivery apparatus on said body tissue at a second site; and,
h) repeating steps d and e.

* * * * *

UNITED STATES PATENT AND TRADEMARK OFFICE
CERTIFICATE OF CORRECTION

PATENT NO. : 5,472,438
DATED : December 5, 1995
INVENTOR(S) : Brian D. Schmit, et. al.

It is certified that error appears in the above-indentified patent and that said Letters Patent is hereby corrected as shown below:

Title page, item [54] in the Title, lines 1 & 2, col. 1, lines 1 & 2-- delete "LAPROSCOPIC" and insert therefor-- LAPAROSCOPIC"--.

Title page, item [54] in the Title, line 2, delete "DAPER" and insert therefor-- PACER--.

Signed and Sealed this

Twelfth Day of March, 1996

Attest:

BRUCE LEHMAN

*Attesting Officer*     *Commissioner of Patents and Trademarks*